US011982646B2

(12) United States Patent
Ida et al.

(10) Patent No.: US 11,982,646 B2
(45) Date of Patent: May 14, 2024

(54) OPTICAL ULTRASONIC WAVE MEASURING APPARATUS, METHOD, AND STORAGE MEDIUM

(71) Applicant: ADVANTEST Corporation, Tokyo (JP)

(72) Inventors: Taiichiro Ida, Gunma (JP); Hideaki Iwazaki, Saitama (JP)

(73) Assignee: ADVANTEST Corporation, Tokyo (JP)

( * ) Notice: Subject to any disclaimer, the term of this patent is extended or adjusted under 35 U.S.C. 154(b) by 425 days.

(21) Appl. No.: 17/333,751

(22) Filed: May 28, 2021

(65) Prior Publication Data

US 2021/0396716 A1 Dec. 23, 2021

(30) Foreign Application Priority Data

Jun. 18, 2020 (JP) ................................ 2020-105344

(51) Int. Cl.
*G01N 29/24* (2006.01)
*A61B 5/00* (2006.01)
*G01N 29/44* (2006.01)

(52) U.S. Cl.
CPC ....... *G01N 29/2418* (2013.01); *A61B 5/0095* (2013.01); *G01N 29/4463* (2013.01);
(Continued)

(58) Field of Classification Search
CPC ................ A61B 5/0033; A61B 5/0095; G01N 2291/011; G01N 2291/02475;
(Continued)

(56) References Cited

U.S. PATENT DOCUMENTS

| 9,506,742 B2* | 11/2016 | Horstmann | ........ G01B 9/02095 |
| 2011/0000299 A1* | 1/2011 | Isobe | .................. G01N 29/265 |
| | | | 73/625 |

(Continued)

FOREIGN PATENT DOCUMENTS

| JP | 11-160429 | 6/1999 |
| JP | 2015-501175 A | 1/2015 |

(Continued)

OTHER PUBLICATIONS

German Office Action, dated Jan. 24, 2022, by the German Patent Office, in German Patent Application No. 10 2021 205 598.2.

(Continued)

*Primary Examiner* — David L Singer
(74) *Attorney, Agent, or Firm* — GREENBLUM & BERNSTEIN, P.L.C.

(57) ABSTRACT

An optical ultrasonic wave measuring apparatus includes an ultrasonic pulse output section, a light pulse output section, a reflected wave measuring section, an optoacoustic wave measuring section, an exceeding time point acquiring section, and a measurement result shifting section. The reflected wave measuring section measures, in correspondence to time, a reflected wave as a result of reflection of the ultrasonic pulse at a measuring target, which may be a skin surface. The optoacoustic wave measuring section measures, in correspondence to time, an optoacoustic wave generated by the light pulse at the measuring target. The exceeding time point acquiring section acquires an exceeding time point at which a measurement result of the reflected wave exceeds a predetermined threshold value. The measurement result shifting section shifts a measurement result of the optoacoustic wave by a first shift time toward the time point of output of the light pulse.

11 Claims, 12 Drawing Sheets

(52) U.S. Cl.
CPC .......... *G01N 2291/011* (2013.01); *G01N 2291/02475* (2013.01); *G01N 2291/02854* (2013.01); *G01N 2291/044* (2013.01); *G01N 2291/045* (2013.01); *G01N 2291/2638* (2013.01)

(58) Field of Classification Search
CPC ... G01N 2291/02854; G01N 2291/044; G01N 2291/045; G01N 2291/2638; G01N 29/2418; G01N 29/4463
See application file for complete search history.

(56) References Cited

U.S. PATENT DOCUMENTS

| | | | |
|---|---|---|---|
| 2012/0200845 A1* | 8/2012 | Rousseau | A61B 5/0093 356/72 |
| 2013/0041247 A1* | 2/2013 | Maswadi | A61B 8/4281 600/407 |
| 2013/0109950 A1 | 5/2013 | Herzog et al. | |
| 2013/0116538 A1 | 5/2013 | Herzog et al. | |
| 2013/0160551 A1* | 6/2013 | Miura | G01N 29/341 73/598 |
| 2013/0168532 A1 | 7/2013 | Schmid et al. | |
| 2013/0276542 A1 | 10/2013 | Herzog et al. | |
| 2013/0279920 A1 | 10/2013 | Herzog | |
| 2013/0281819 A1 | 10/2013 | Schmid | |
| 2013/0289381 A1 | 10/2013 | Oraevsky et al. | |
| 2013/0296683 A1 | 11/2013 | Herzog et al. | |
| 2013/0296684 A1 | 11/2013 | Miller et al. | |
| 2013/0296701 A1 | 11/2013 | Zalev et al. | |
| 2013/0301380 A1 | 11/2013 | Oraevsky et al. | |
| 2013/0303875 A1 | 11/2013 | Joy et al. | |
| 2013/0304405 A1 | 11/2013 | Schmid et al. | |
| 2013/0334421 A1* | 12/2013 | Itsuji | G01J 3/42 250/341.8 |
| 2013/0335441 A1 | 12/2013 | Zalev et al. | |
| 2013/0336551 A1 | 12/2013 | Clingman et al. | |
| 2013/0338475 A1 | 12/2013 | Herzog et al. | |
| 2013/0338501 A1 | 12/2013 | Clingman | |
| 2014/0005544 A1 | 1/2014 | Zalev et al. | |
| 2014/0012124 A1 | 1/2014 | Zalev | |
| 2014/0036053 A1 | 2/2014 | Clingman et al. | |
| 2014/0036091 A1 | 2/2014 | Zalev et al. | |
| 2014/0039293 A1 | 2/2014 | Oraevsky et al. | |
| 2014/0093150 A1 | 4/2014 | Zalev et al. | |
| 2014/0185899 A1 | 7/2014 | Zalev et al. | |
| 2014/0194723 A1 | 7/2014 | Herzog et al. | |
| 2014/0206978 A1 | 7/2014 | Ackerman et al. | |
| 2014/0208856 A1 | 7/2014 | Schmid | |
| 2014/0219530 A1 | 8/2014 | Zalev | |
| 2014/0249414 A1 | 9/2014 | Herzog et al. | |
| 2014/0309515 A1* | 10/2014 | Ida | A61B 5/0095 600/407 |
| 2014/0350402 A1 | 11/2014 | Hirota et al. | |
| 2015/0018662 A1 | 1/2015 | Ackerman, III et al. | |
| 2015/0047433 A1* | 2/2015 | Ida | G01N 29/343 73/645 |
| 2015/0075287 A1 | 3/2015 | Herzog et al. | |
| 2015/0075288 A1* | 3/2015 | Ida | G01N 21/1702 73/655 |
| 2015/0297090 A1 | 10/2015 | Herzog et al. | |
| 2015/0327769 A1* | 11/2015 | Baba | A61B 8/4281 600/407 |
| 2016/0199037 A1 | 7/2016 | Clingman et al. | |
| 2016/0296121 A1 | 10/2016 | Herzog et al. | |
| 2016/0317034 A1 | 11/2016 | Zalev et al. | |
| 2016/0317038 A1 | 11/2016 | Zalev et al. | |
| 2017/0000354 A1 | 1/2017 | Zalev et al. | |
| 2017/0014101 A1 | 1/2017 | Oraevsky et al. | |
| 2017/0035388 A1 | 2/2017 | Herzog et al. | |
| 2017/0052254 A1 | 2/2017 | Tateyama | |
| 2017/0069089 A1 | 3/2017 | Zalev | |
| 2017/0100040 A1 | 4/2017 | Zalev et al. | |
| 2017/0108429 A1 | 4/2017 | Schmid | |
| 2017/0150890 A1 | 6/2017 | Herzog et al. | |
| 2017/0156602 A1 | 6/2017 | Ackerman, III et al. | |
| 2017/0296151 A1 | 10/2017 | Herzog et al. | |
| 2017/0322071 A1 | 11/2017 | Schmid et al. | |
| 2017/0332915 A1 | 11/2017 | Herzog et al. | |
| 2017/0332916 A1 | 11/2017 | Zalev et al. | |
| 2018/0061050 A1 | 3/2018 | Zalev et al. | |
| 2018/0078144 A1 | 3/2018 | Schmid | |
| 2018/0235477 A1 | 8/2018 | Hirota et al. | |
| 2019/0064120 A1* | 2/2019 | Yamamoto | G01N 29/0645 |
| 2019/0150750 A1 | 5/2019 | Zalev et al. | |
| 2019/0192006 A1 | 6/2019 | Herzog et al. | |
| 2019/0216332 A1 | 7/2019 | Zalev et al. | |
| 2019/0266725 A1 | 8/2019 | Zalev et al. | |
| 2020/0085345 A1 | 3/2020 | Nanaumi et al. | |
| 2023/0172586 A1* | 6/2023 | Clingman | A61B 8/4494 600/407 |

FOREIGN PATENT DOCUMENTS

| | | | | |
|---|---|---|---|---|
| JP | 2015073576 A | * | 4/2015 | ........... A61B 5/0095 |
| JP | 2017-038917 A | | 2/2017 | |
| JP | 2020-39809 | | 3/2020 | |
| WO | WO-2013006046 A1 | * | 1/2013 | ........... G01N 29/069 |
| WO | 2013/121751 A1 | | 8/2013 | |
| WO | 2019/111568 | | 6/2019 | |
| WO | WO-2019111568 A1 | * | 6/2019 | ........... A61B 5/0095 |

OTHER PUBLICATIONS

Adrian Taruttis et al., "Optoacoustic Imaging of Human Vasculature: Feasibility by Using a Handheld Probe", Radiology: vol. 281, No. 1, Oct. 2016, pp. 256-263.
Office Action issued by the China National Intellectual Property Administration (CNIPA) in Chinese Patent Application No. 202110514935.1, dated Jul. 26, 2023.
English language translation of German Office Action received in Patent Application No. 10 2021 205 598.2, dated Jan. 24, 2022.
English language translation of Chinese Office Action received in Patent Application No. 202110514935.1, dated Jul. 26, 2023.
Japan Office Action received in Patent Application No. 2020-105344, dated Nov. 6, 2023.
China Office Action issued in CN Application No. 202110514935.1, dated Feb. 29, 2024.

\* cited by examiner

OPTICAL ULTRASONIC WAVE MEASURING APPARATUS, METHOD, AND STORAGE MEDIUM

BACKGROUND OF THE INVENTION

Field of the Invention

The present invention relates to measuring reflected ultrasonic waves and optoacoustic waves.

Description of the Related Art

Upon irradiation of light absorbers with light pulses of a specific wavelength, the light energy is absorbed, as known conventionally. This causes instantaneous adiabatic expansion within the light absorbers and thereby ultrasonic waves to be generated therefrom. By receiving and imaging the ultrasonic waves with a sensor such as a piezoelectric element, it is possible to know the three-dimensional distribution of the light absorbers. There has also been known providing ultrasonic waves to a measuring target and measuring reflected waves therefrom to image the interior of the measuring target (see Japanese Patent Application Publication No. 2017-038917, Japanese Patent Application Publication No. 2015-501175, and WO2013/121751).

SUMMARY OF THE INVENTION

However, when trying to measure a measuring target (e.g. skin) with such a related art as described above, it is necessary to bring a measuring apparatus into contact with the measuring target. The surface of the measuring target then bulges due to the pressure within the measuring target. The bulging of the measuring target may cause fluctuation in the depth position of an object (e.g. blood vessel) within the measuring target.

It is hence an object of the present invention to measure a measuring target while compensating for fluctuation in the surface profile of the measuring target when a measuring apparatus is brought into contact with the measuring target.

According to the present invention, an optical ultrasonic wave measuring apparatus includes: an ultrasonic pulse output section arranged to output an ultrasonic pulse; a light pulse output section arranged to output a light pulse; a reflected wave measuring section arranged to measure, in correspondence to time, a reflected wave as a result of reflection of the ultrasonic pulse at a measuring target; an optoacoustic wave measuring section arranged to measure, in correspondence to time, an optoacoustic wave generated by the light pulse at the measuring target; an exceeding time point acquiring section arranged to acquire an exceeding time point at which a measurement result of the reflected wave exceeds a predetermined threshold value; and a measurement result shifting section arranged to shift a measurement result of the optoacoustic wave by a first shift time toward the time point of output of the light pulse, wherein if the time point in the measurement result of the optoacoustic wave corresponding to the exceeding time point is defined as a correspondence time point, the first shift time is equal to or shorter than a correspondence time between the time point of output of the light pulse and the correspondence time point.

According to the present invention, an ultrasonic pulse output section outputs an ultrasonic pulse. A light pulse output section outputs a light pulse. A reflected wave measuring section measures, in correspondence to time, a reflected wave as a result of reflection of the ultrasonic pulse at a measuring target. An optoacoustic wave measuring section measures, in correspondence to time, an optoacoustic wave generated by the light pulse at the measuring target. An exceeding time point acquiring section acquires an exceeding time point at which a measurement result of the reflected wave exceeds a predetermined threshold value. A measurement result shifting section shifts a measurement result of the optoacoustic wave by a first shift time toward the time point of output of the light pulse. The time point in the measurement result of the optoacoustic wave corresponding to the exceeding time point is defined as a correspondence time point. The first shift time is equal to or shorter than a correspondence time between the time point of output of the light pulse and the correspondence time point.

According to the optical ultrasonic wave measuring apparatus of the present invention, the difference between the first shift time and the correspondence time may be equal for a plurality of optoacoustic waves obtained for a plurality of sites in the measuring target.

According to the optical ultrasonic wave measuring apparatus of the present invention, the measurement result shifting section may be arranged to shift the measurement result of the reflected wave by a second shift time toward the time point of output of the ultrasonic pulse, and the second shift time may be equal to or shorter than an exceeding time between the reflection of the ultrasonic pulse at the surface boundary of the measuring target and the exceeding time point.

According to the optical ultrasonic wave measuring apparatus of the present invention, the difference between the exceeding time and the second shift time may be equal for a plurality of reflected waves obtained for a plurality of sites in the measuring target.

According to the optical ultrasonic wave measuring apparatus of the present invention, the first shift time and the second shift time may be equal to each other.

According to the optical ultrasonic wave measuring apparatus of the present invention, the exceeding time point and the correspondence time point may be at the same time point.

According to the present invention, the optical ultrasonic wave measuring apparatus may further include an image displaying section arranged to display an image of the measuring target based on an output from the measurement result shifting section.

According to the optical ultrasonic wave measuring apparatus of the present invention, the ultrasonic pulse output section and the light pulse output section may be arranged to scan the measuring target, and the direction of the scanning may be orthogonal to the direction of output of the ultrasonic pulse and the light pulse.

According to the present invention, the optical ultrasonic wave measuring apparatus may further include a plurality of light pulse output sections, wherein the light pulse output sections may be arranged to output light pulses of different wavelengths.

The present invention is an optical ultrasonic wave measuring method including: outputting an ultrasonic pulse; outputting a light pulse; measuring, in correspondence to time, a reflected wave as a result of reflection of the ultrasonic pulse at a measuring target; measuring, in correspondence to time, an optoacoustic wave generated by the light pulse at the measuring target; acquiring an exceeding time point at which a measurement result of the reflected wave exceeds a predetermined threshold value; and shifting a measurement result of the optoacoustic wave by a first shift time toward the time point of output of the light pulse, wherein if the time point in the measurement result of the optoacoustic wave corresponding to the exceeding time point is defined as a correspondence time point, the first shift time is equal to or shorter than a correspondence time between the time point of output of the light pulse and the correspondence time point.

The present invention is a program of instructions for execution by a computer to perform an optical ultrasonic wave measuring process of an optical ultrasonic wave measuring apparatus including: an ultrasonic pulse output section arranged to output an ultrasonic pulse; a light pulse output section arranged to output a light pulse; a reflected wave measuring section arranged to measure, in correspondence to time, a reflected wave as a result of reflection of the ultrasonic pulse at a measuring target; and an optoacoustic wave measuring section arranged to measure, in correspondence to time, an optoacoustic wave generated by the light pulse at the measuring target, the process including: acquiring an exceeding time point at which a measurement result of the reflected wave exceeds a predetermined threshold value; and shifting a measurement result of the optoacoustic wave by a first shift time toward the time point of output of the light pulse, wherein if the time point in the measurement result of the optoacoustic wave corresponding to the exceeding time point is defined as a correspondence time point, the first shift time is equal to or shorter than a correspondence time between the time point of output of the light pulse and the correspondence time point.

The present invention is a non-transitory computer-readable medium having a program of instructions for execution by a computer to perform an optical ultrasonic wave measuring process of an optical ultrasonic wave measuring apparatus including: an ultrasonic pulse output section arranged to output an ultrasonic pulse; a light pulse output section arranged to output a light pulse; a reflected wave measuring section arranged to measure, in correspondence to time, a reflected wave as a result of reflection of the ultrasonic pulse at a measuring target; and an optoacoustic wave measuring section arranged to measure, in correspondence to time, an optoacoustic wave generated by the light pulse at the measuring target, the process including: acquiring an exceeding time point at which a measurement result of the reflected wave exceeds a predetermined threshold value; and shifting a measurement result of the optoacoustic wave by a first shift time toward the time point of output of the light pulse, wherein if the time point in the measurement result of the optoacoustic wave corresponding to the exceeding time point is defined as a correspondence time point, the first shift time is equal to or shorter than a correspondence time between the time point of output of the light pulse and the correspondence time point.

BRIEF DESCRIPTION OF THE DRAWINGS

FIG. 4 is an enlarged cross-sectional view of the measuring target 2 in the vicinity of the measuring unit 100 when the measuring unit 100 is almost directly above the blood vessel 24a;

FIGS. 5 (a)-5 (c) show a waveform of the reflected wave US (FIG. 5 (a)), a waveform of the optoacoustic wave AW1 (or AW2) (FIG. 5 (b)), and a distance-converted version of the horizontal axis (time) of the waveforms (FIG. 5 (c)) when the measuring unit 100 is directly above the blood vessel 24a;

DESCRIPTION OF THE PREFERRED EMBODIMENTS

A preferred embodiment of the present invention will hereinafter be described with reference to the accompanying drawings.

Figure 1:
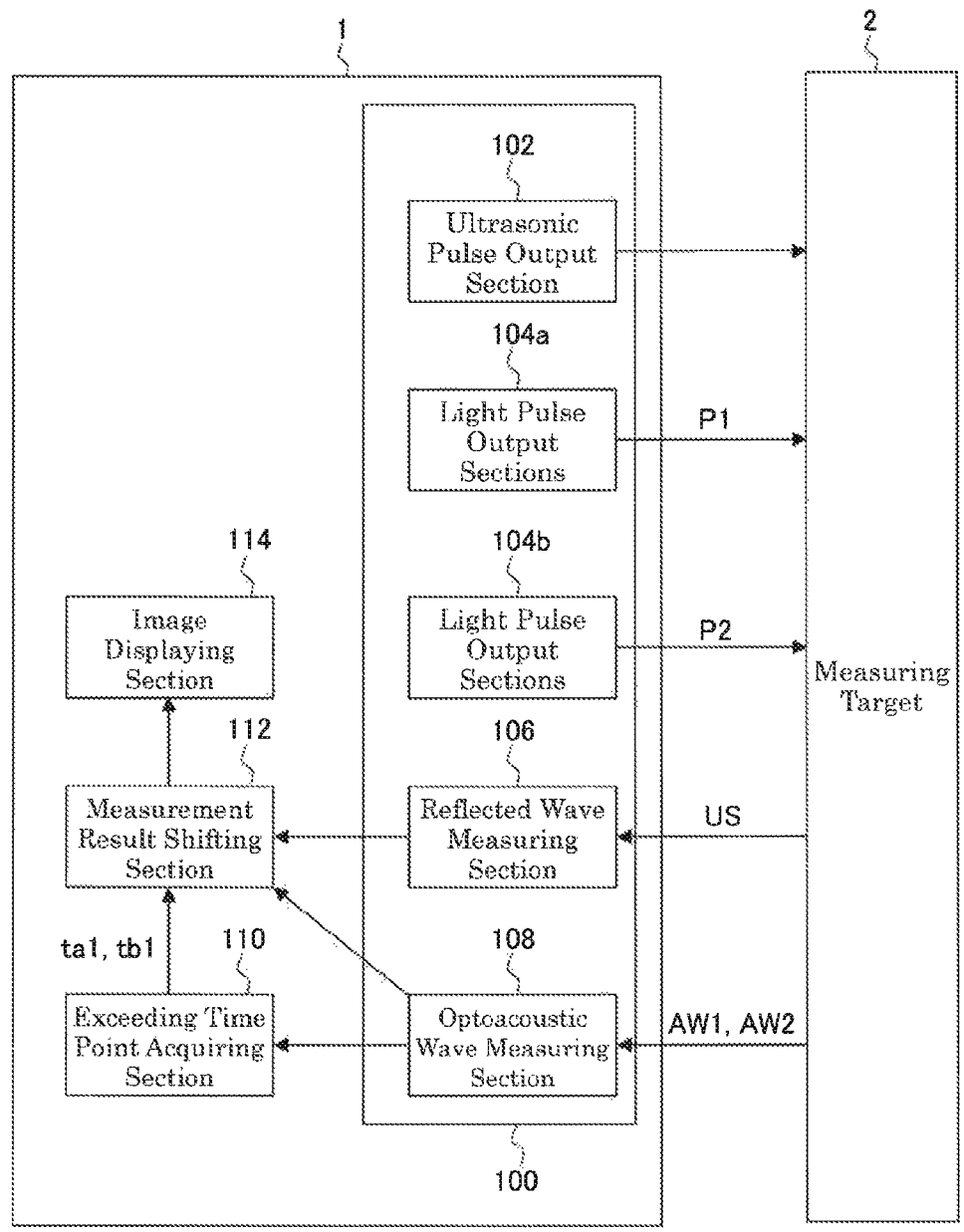
FIG. 1 is a functional block diagram showing the configuration of an optical ultrasonic wave measuring apparatus 1 according to an embodiment of the present invention.

FIG. 1 is a functional block diagram showing the configuration of an optical ultrasonic wave measuring apparatus 1 according to an embodiment of the present invention. The optical ultrasonic wave measuring apparatus 1 according to the embodiment of the present invention is intended for measuring a measuring target 2 (including skin, for example, but no limited thereto) and includes a measuring unit 100, an exceeding time point acquiring section 110, a measurement result shifting section 112, and an image displaying section 114. It is noted that the embodiment of the present invention will hereinafter be described for the case where the measuring target 2 is skin.

Figure 2:
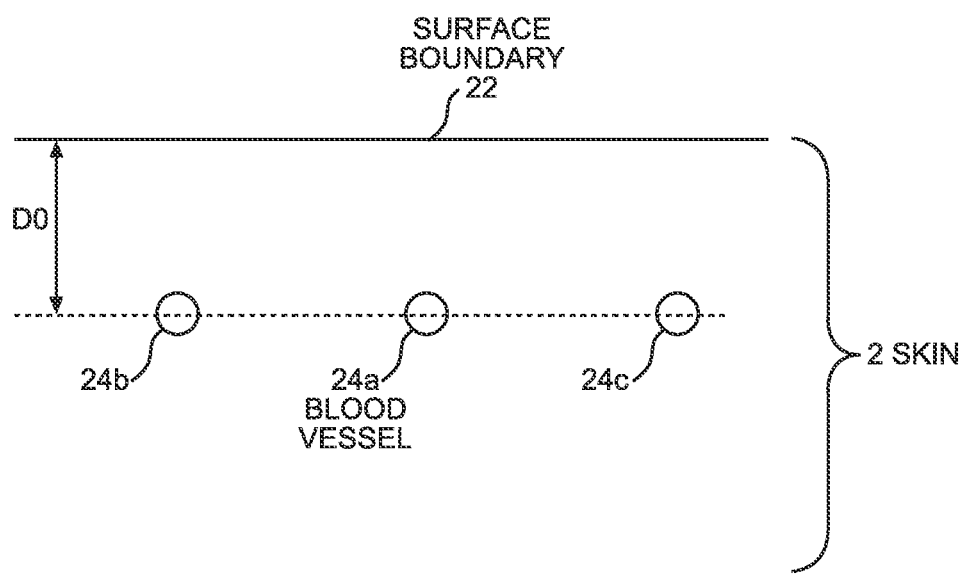
FIG. 2 is a cross-sectional view of the measuring target (skin) 2 with nothing in contact therewith.
Figure 11A:
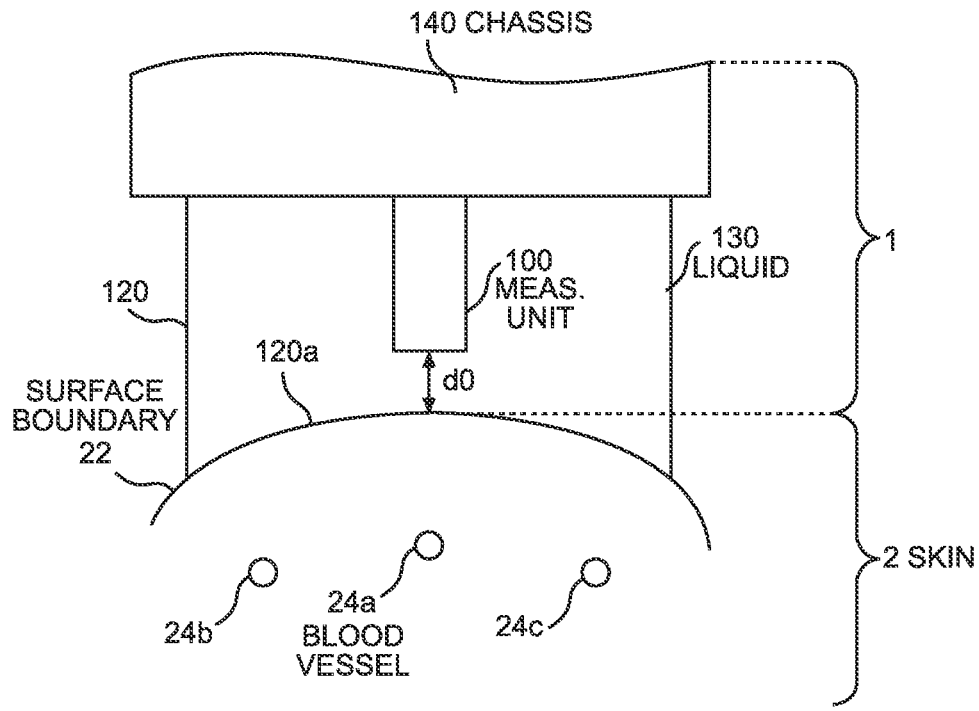
FIGS. 11 (a) and 11 (b) are cross-sectional views of the optical ultrasonic wave measuring apparatus 1 and the measuring target (skin) 2 with the optical ultrasonic wave measuring apparatus 1 in contact with the measuring target (skin) 2, showing a state where the measuring unit 100 is almost directly above a blood vessel 24a (FIG. 11 (a)) and a state where the measuring unit 100 is almost directly above a blood vessel 24b (FIG. 11 (b))
Figure 11B:
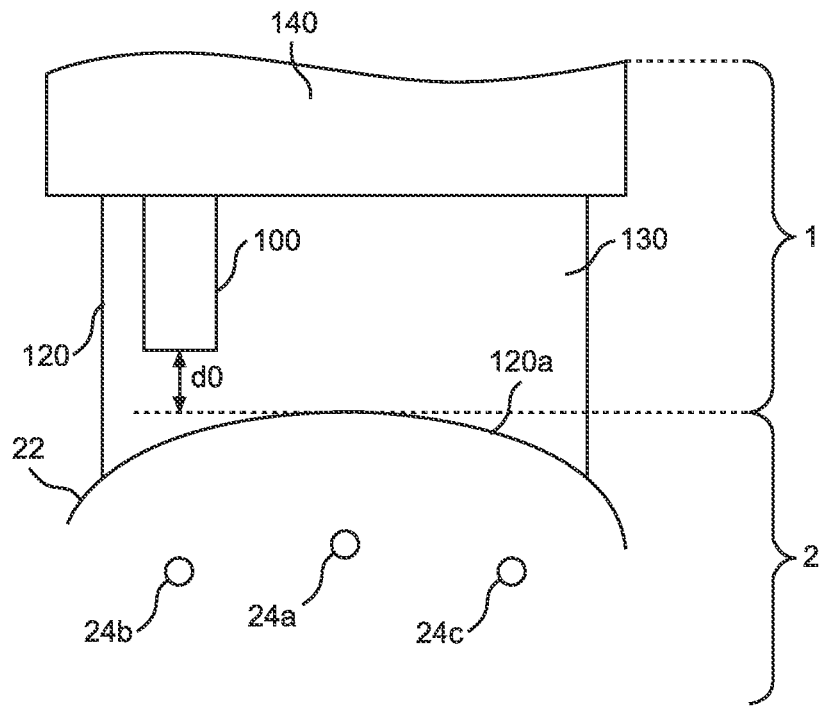

FIG. 2 is a cross-sectional view of the measuring target (skin) 2 with nothing in contact therewith. FIG. 11 is a cross-sectional view of the optical ultrasonic wave measuring apparatus 1 and the measuring target (skin) 2 with the optical ultrasonic wave measuring apparatus 1 in contact with the measuring target (skin) 2, showing a state where the measuring unit 100 is almost directly above a blood vessel 24a (FIG. 11 (a)) and a state where the measuring unit 100 is almost directly above a blood vessel 24b (FIG. 11 (b)).

Referring to FIG. 2, with nothing in contact with the measuring target (skin) 2, it is given that the surface boundary 22 of the measuring target 2 (surface of the skin) is horizontal and the blood vessels 24a, 24b, 24c within the measuring target 2 all have a depth of D0 from the surface boundary 22. It is noted that the blood vessel 24a is between the blood vessel 24b and the blood vessel 24c.

Referring to FIG. 11, the optical ultrasonic wave measuring apparatus 1 includes the measuring unit 100, a case 120, liquid 130, and a chassis 140. The case 120 houses the measuring unit 100 therein and its interior is filled with the liquid 130 (e.g. water). A thin film 120a is arranged at the bottom of the case 120. The thin film 120a is in contact with the surface boundary 22. The surface boundary 22 then has a curvature to be convex upward. The chassis 140 is arranged on top of the measuring unit 100 and the case 120 and houses the exceeding time point acquiring section 110, the measurement result shifting section 112, and the image displaying section 114 therein. It is noted that the difference in height between the measuring unit 100 and the highest point of the surface boundary 22 is defined as d0.

Figure 3:
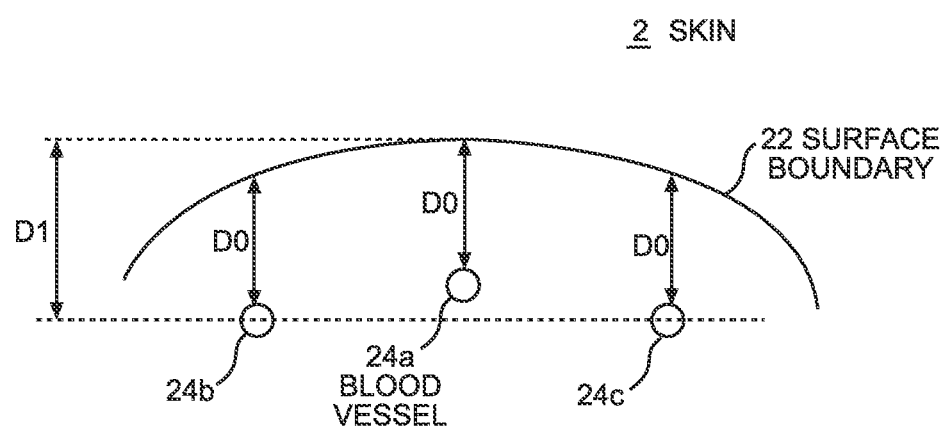
FIG. 3 is an enlarged cross-sectional view of the measuring target 2 with the optical ultrasonic wave measuring apparatus 1 in contact with the measuring target 2.

FIG. 3 is an enlarged cross-sectional view of the measuring target 2 with the optical ultrasonic wave measuring apparatus 1 in contact with the measuring target 2. Since the surface boundary 22 has a curvature to be convex upward, the blood vessel 24a is at a position higher than those of the blood vessel 24b and the blood vessel 24c. However, all of the blood vessels 24a, 24b, 24c still have a depth of D0 from the surface boundary 22. The depth of the blood vessel 24b and the blood vessel 24c from the highest portion of the surface boundary 22 is here defined as D1.

The blood vessels 24a, 24b, 24c are positioned at such different heights as described above with the optical ultrasonic wave measuring apparatus 1 in contact with the measuring target 2 (see FIG. 3), though naturally supposed to be positioned at the same height (see FIG. 2). Even measuring the positions of the blood vessels 24a, 24b, 24c in this state and displaying them in an image cannot lead to knowing their natural positions.

Referring to FIG. 1, the measuring unit 100 has an ultrasonic pulse output section 102, light pulse output sections 104a, 104b, a reflected wave measuring section 106, and an optoacoustic wave measuring section 108.

The ultrasonic pulse output section 102 is arranged to output an ultrasonic pulse. The multiple light pulse output sections 104a, 104b are arranged to output light pulses. It is noted that light pulses output from the respective light pulse output sections 104a, 104b have their respective different wavelengths. The number of light pulse output sections may, however, be three or more or may be only one.

The reflected wave measuring section 106 is arranged to measure, in correspondence to time, a reflected wave US as a result of reflection of the ultrasonic pulse at the measuring target 2. The optoacoustic wave measuring section 108 is arranged to measure, in correspondence to time, optoacoustic waves AW1, AW2 generated by the light pulses at the measuring target 2. It is noted that the optoacoustic wave AW1 is generated at the measuring target 2 by the light pulse P1 output from the light pulse output section 104a. It is also noted that the optoacoustic wave AW2 is generated at the measuring target 2 by the light pulse P2 output from the light pulse output section 104b. The reflected wave measuring section 106 and the optoacoustic wave measuring section 108 are, for example, piezoelectric elements.

The ultrasonic pulse output section 102 and the light pulse output sections 104a, 104b of the measuring unit 100 are arranged to scan the measuring target 2.

Figure 10:
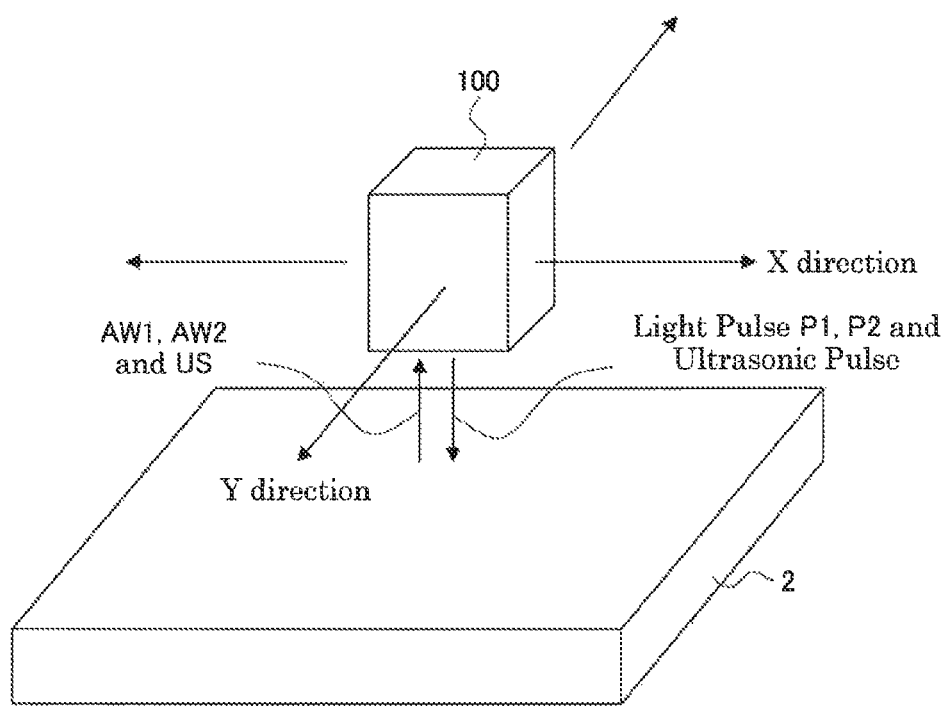
FIG. 10 is a perspective view showing an example of scanning of the measuring target 2 by the measuring unit 100.

FIG. 10 is a perspective view showing an example of scanning of the measuring target 2 by the measuring unit 100. However, in FIG. 10, the case 120, the liquid 130, and the chassis 140 are not shown. The ultrasonic pulse output section 102 and the light pulse output sections 104a, 104b of the measuring unit 100 are arranged to output light pulses P1, P2 and an ultrasonic pulse and perform scanning in the direction (X direction and Y direction) orthogonal to the direction of the output. This causes the measuring unit 100 to be almost directly above the blood vessel 24a, the blood vessel 24b, or the blood vessel 24c.

The embodiment of the present invention will hereinafter be described separately for (1) the case where the measuring unit 100 is almost directly above the blood vessel 24a and (2) the case where the measuring unit 100 is almost directly above the blood vessel 24b. It is noted that the case where the measuring unit 100 is almost directly above the blood vessel 24c is identical to the case where the measuring unit 100 is almost directly above the blood vessel 24b and therefore will not be described.

(1) Case where the Measuring Unit 100 is Almost Directly Above the Blood Vessel 24a (See FIG. 11 (a))

Figure 4:
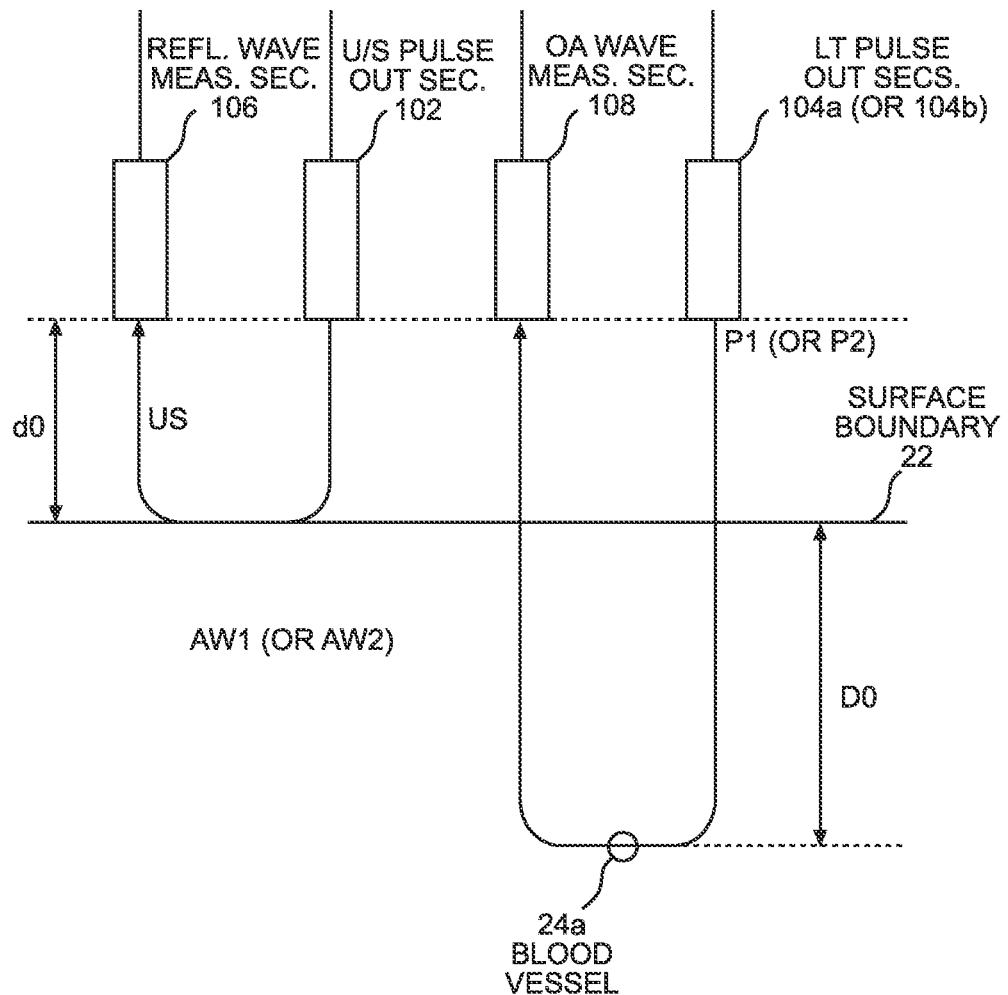

FIG. 4 is an enlarged cross-sectional view of the measuring target 2 in the vicinity of the measuring unit 100 when the measuring unit 100 is almost directly above the blood vessel 24a.

An ultrasonic pulse output from the ultrasonic pulse output section 102 is reflected mainly by the surface boundary 22 and the intensity of a reflected wave US is measured by the reflected wave measuring section 106. The distance between the ultrasonic pulse output section 102 as well as the reflected wave measuring section 106 and the surface boundary 22 is d0. It is noted that the distance between the light pulse output sections 104a, 104b as well as the optoacoustic wave measuring section 108 and the surface boundary 22 is also d0.

The intensity of an optoacoustic wave AW1 (or AW2) generated at the blood vessel 24a of the measuring target 2 by a light pulse P1 (or P2) output from the light pulse output section 104a (or 104b) is measured by the optoacoustic wave measuring section 108. The depth of the blood vessel 24a from the surface boundary 22 is D0.

Figure 5:
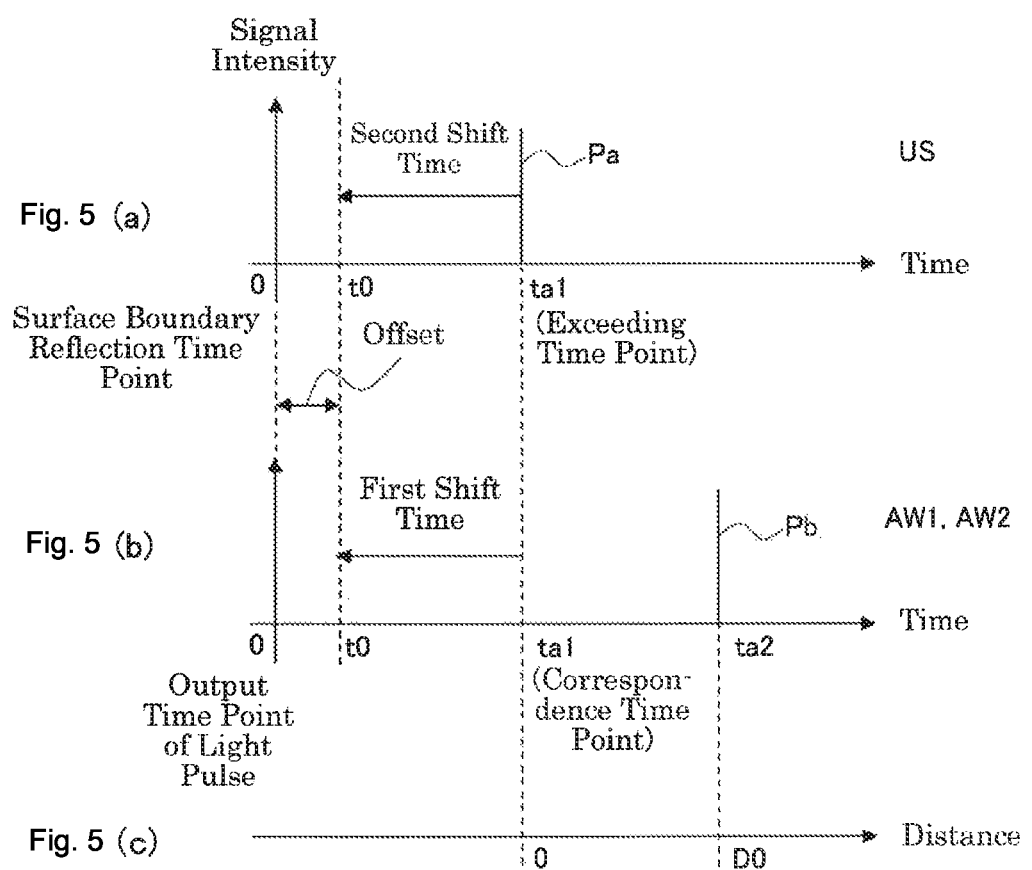

FIG. 5 shows a waveform of the reflected wave US (FIG. 5 (a)), a waveform of the optoacoustic wave AW1 (or AW2) (FIG. 5 (b)), and a distance-converted version of the horizontal axis (time) of the waveforms (FIG. 5 (c)) when the measuring unit 100 is directly above the blood vessel 24a.

In FIG. 5 (a), the vertical axis represents signal intensity, while the horizontal axis represents time, with the origin representing the time point at which the ultrasonic pulse is reflected by the surface boundary 22. At the time point ta1 at which an ultrasonic pulse Pa is received by the reflected wave measuring section 106 of the measuring unit 100, the measurement result of the reflected wave US (i.e. the signal intensity of the ultrasonic pulse Pa) exceeds a predetermined threshold value. It is noted that the predetermined threshold value is set such that (1) the intensity of the reflected wave US, if reflected by the surface boundary 22, exceeds the predetermined threshold value, while (2) the intensity of the reflected wave US, if not reflected by the surface boundary 22, does not exceed the predetermined threshold value. The exceeding time point acquiring section 110 is arranged to acquire an exceeding time point ta1 at which the measurement result of the reflected wave US exceeds the predetermined threshold value.

Since the signal intensity of the ultrasonic pulse Pa exceeds the predetermined threshold value, it is recognized that the reflection by the surface boundary 22 is detected by the reflected wave measuring section 106 at the time point (exceeding time point ta1) at which the ultrasonic pulse Pa is received. Accordingly, the distance d0 between the reflected wave measuring section 106 and the surface boundary 22 is obtained by multiplying the time (referred to as exceeding time) between the reflection of the ultrasonic pulse at the surface boundary 22 of the measuring target 2 and the exceeding time point ta1 by the speed of sound Vs (Vs·ta1=d0) (where the exceeding time is ta1).

In FIG. 5 (b), the vertical axis represents signal intensity, while the horizontal axis represents time, with the origin representing the time point at which the light pulse P1 (or P2) is output. The output light pulse P1 (or P2) reaches the blood vessel 24a at almost the same time as the output. Accordingly, the time point at which the light pulse P1 (or P2) is output can be viewed the same as the time point at which the optoacoustic wave AW1 (or AW2) is output. Note here that the origin in FIG. 5 (b) (the time point at which the light pulse P1 (or P2) is output) and the origin in FIG. 5 (a) (the time point at which the ultrasonic pulse is reflected by the surface boundary 22) are at the same time point. The time point at which the optoacoustic pulse Pb of the optoacoustic wave AW1 (or AW2) generated at the blood vessel 24a is received by the optoacoustic wave measuring section 108 of the measuring unit 100 is defined as ta2. This results in Vs·ta2=d0+D0.

FIG. 5 (c) provides a horizontal axis, showing that if the position corresponding to the exceeding time point ta1 (representing the position of the surface boundary 22) is set 0, the position corresponding to the time point ta2 at which the optoacoustic pulse Pb is received (representing the depth of the blood vessel 24a) is D0 (=Vs·(ta2−ta1)).

The measurement result shifting section 112 is arranged to shift the measurement result of the optoacoustic waves AW1, AW2 by a first shift time toward the time point of output of the light pulses (see FIG. 5 (b)). The time point in the measurement result of the optoacoustic wave AW1 (or AW2) corresponding to the exceeding time point ta1 is here defined as a correspondence time point. The first shift time is then equal to or shorter than a correspondence time between the time point of output of the light pulses and the correspondence time point. It is noted that since the origin in FIG. 5 (b) and the origin in FIG. 5 (a) are at the same time point, the correspondence time point is ta1, which is the same as the exceeding time point ta1. The correspondence time is thus ta1.

The measurement result shifting section 112 is arranged to shift the measurement result of the reflected wave US by a second shift time toward the time point of output of the ultrasonic pulse (see FIG. 5 (a)). It is noted that the time point of output of the ultrasonic pulse precedes the time point at which the ultrasonic pulse is reflected by the surface boundary 22. Accordingly, the measurement result of the reflected wave US, when shifted toward the time point of output of the ultrasonic pulse, will also be shifted toward the time point at which the ultrasonic pulse is reflected by the surface boundary 22. It is noted that the second shift time is equal to or shorter than the exceeding time ta1.

It is noted that the first shift time and the second shift time are equal to each other. The difference t0 between the correspondence time ta1 and the first shift time is also equal to the difference t0 between the exceeding time ta1 and the second shift time (called offset).

Figure 6:
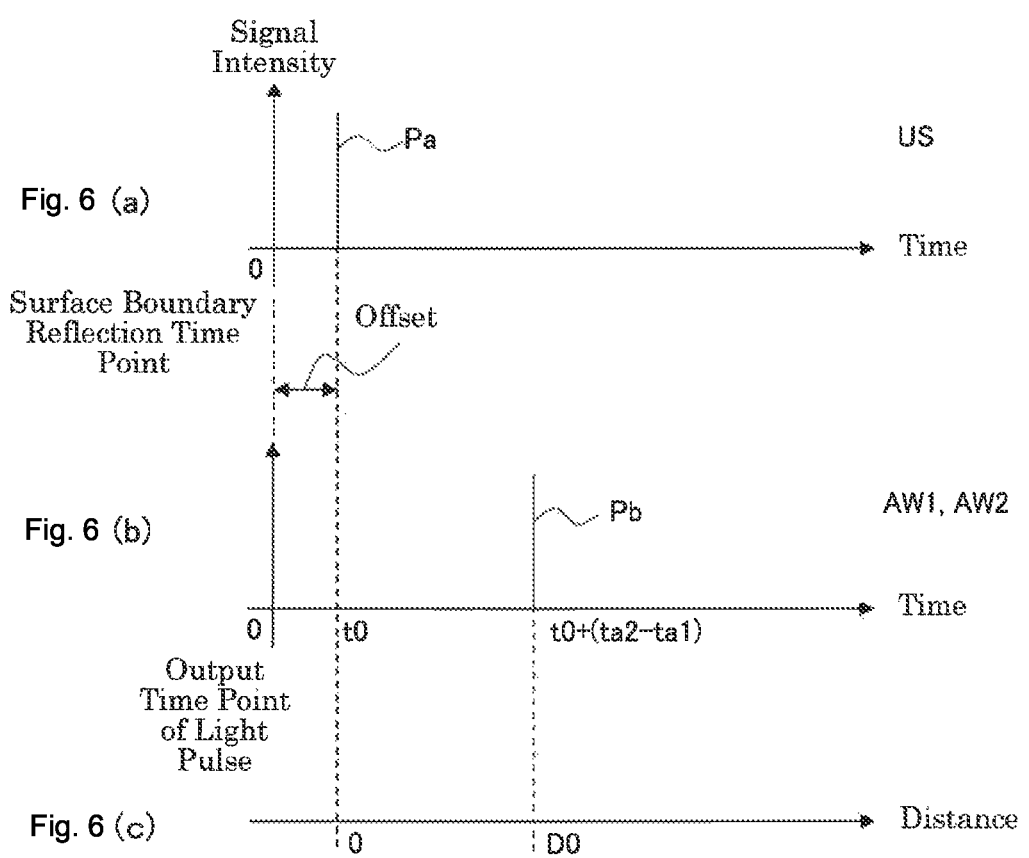
FIGS. 6 (a)-6 (c) show a shifted waveform of the reflected wave US according to FIG. 5 (a) (FIG. 6 (a)), a shifted waveform of the optoacoustic wave AW1 (or AW2) according to FIG. 5 (b) (FIG. 6 (b)), and a distance-converted version of the horizontal axis (time) of the waveforms (FIG. 6 (c))

FIG. 6 shows a shifted waveform of the reflected wave US according to FIG. 5 (a) (FIG. 6 (a)), a shifted waveform of the optoacoustic wave AW1 (or AW2) according to FIG. 5 (b) (FIG. 6 (b)), and a distance-converted version of the horizontal axis (time) of the waveforms (FIG. 6 (c)).

Referring to FIG. 6 (a), the measurement result shifting section 112 is arranged to shift the ultrasonic pulse Pa to the offset t0. Referring to FIG. 6 (b), the measurement result shifting section 112 is arranged to shift the optoacoustic pulse Pb to the time point t0+(ta2−ta1). FIG. 6 (c) provides a horizontal axis, showing that if the position corresponding to the offset t0 (representing the position of the surface boundary 22) is set 0, the position corresponding to the time point t0+(ta2−ta1) to which the optoacoustic pulse Pb is shifted (representing the depth of the blood vessel 24a) is D0 (=Vs·(t0+(ta2−ta1)−t0)=Vs·(ta2−ta1)).

The image displaying section 114 is arranged to display an image of the measuring target 2 based on an output from the measurement result shifting section 112.

Figure 9:
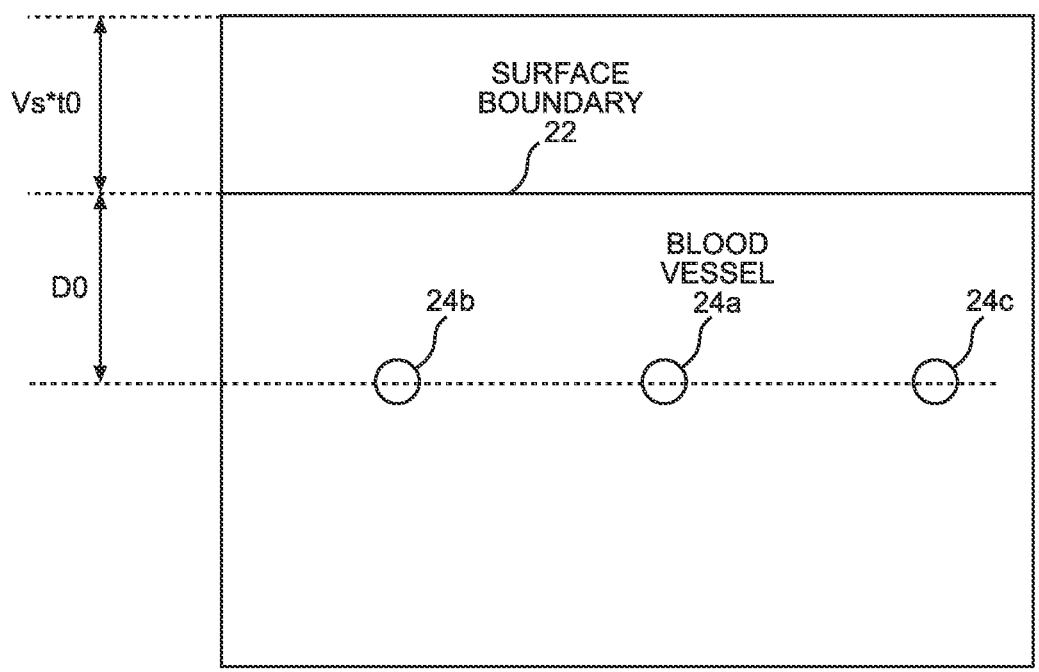
FIG. 9 shows an image that the image displaying section 114 displays.

FIG. 9 shows an image that the image displaying section 114 displays. The upper end of the image corresponds to the origins in FIGS. 6 (a) and 6 (b). Here, the position corresponding to the offset t0 where the ultrasonic pulse Pa exists represents the position of the surface boundary 22. The image of the surface boundary 22 then exists at a position apart from the upper end of the image by Vs·t0. Further, the position corresponding to the time point t0+(ta2−ta1) where the optoacoustic pulse Pb exists represents the position of the blood vessel 24a. The image of the blood vessel 24a then exists at a position apart from the image of the surface boundary 22 by D0.

(2) Case where the Measuring Unit 100 is Almost Directly Above the Blood Vessel 24b (See FIG. 11 (b))

Figure 12:
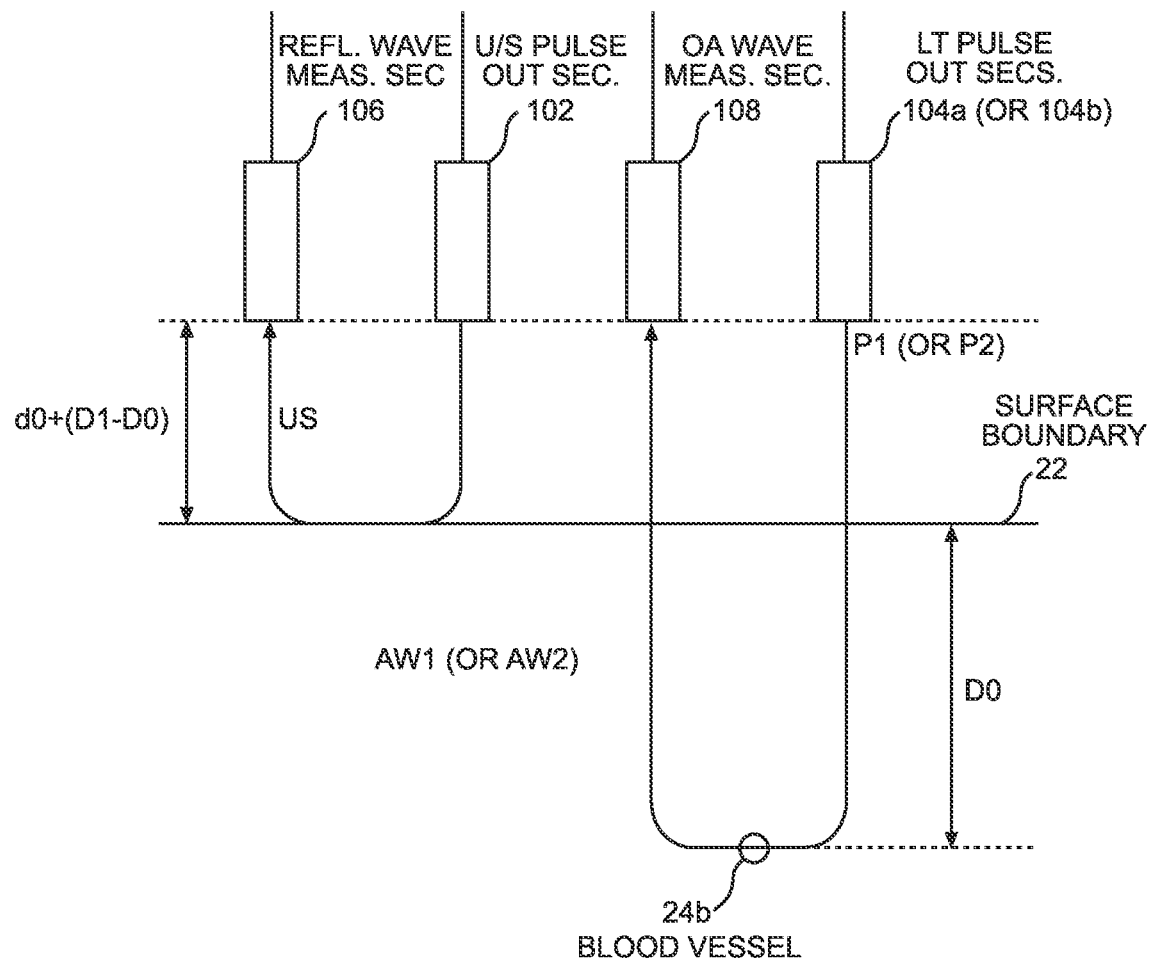
FIG. 12 is an enlarged cross-sectional view of the measuring target 2 in the vicinity of the measuring unit 100 when the measuring unit 100 is almost directly above the blood vessel 24b.

FIG. 12 is an enlarged cross-sectional view of the measuring target 2 in the vicinity of the measuring unit 100 when the measuring unit 100 is almost directly above the blood vessel 24b.

An ultrasonic pulse output from the ultrasonic pulse output section 102 is reflected mainly by the surface boundary 22 and the intensity of a reflected wave US is measured by the reflected wave measuring section 106. The distance between the ultrasonic pulse output section 102 as well as the reflected wave measuring section 106 and the surface boundary 22 is d0+(D1−D0). It is noted that the distance between the light pulse output sections 104a, 104b as well as the optoacoustic wave measuring section 108 and the surface boundary 22 is also d0+(D1−D0).

The intensity of an optoacoustic wave AW1 (or AW2) generated at the blood vessel 24b of the measuring target 2 by a light pulse P1 (or P2) output from the light pulse output section 104a (or 104b) is measured by the optoacoustic wave measuring section 108. The depth of the blood vessel 24b from the surface boundary 22 is D0.

Figure 7:
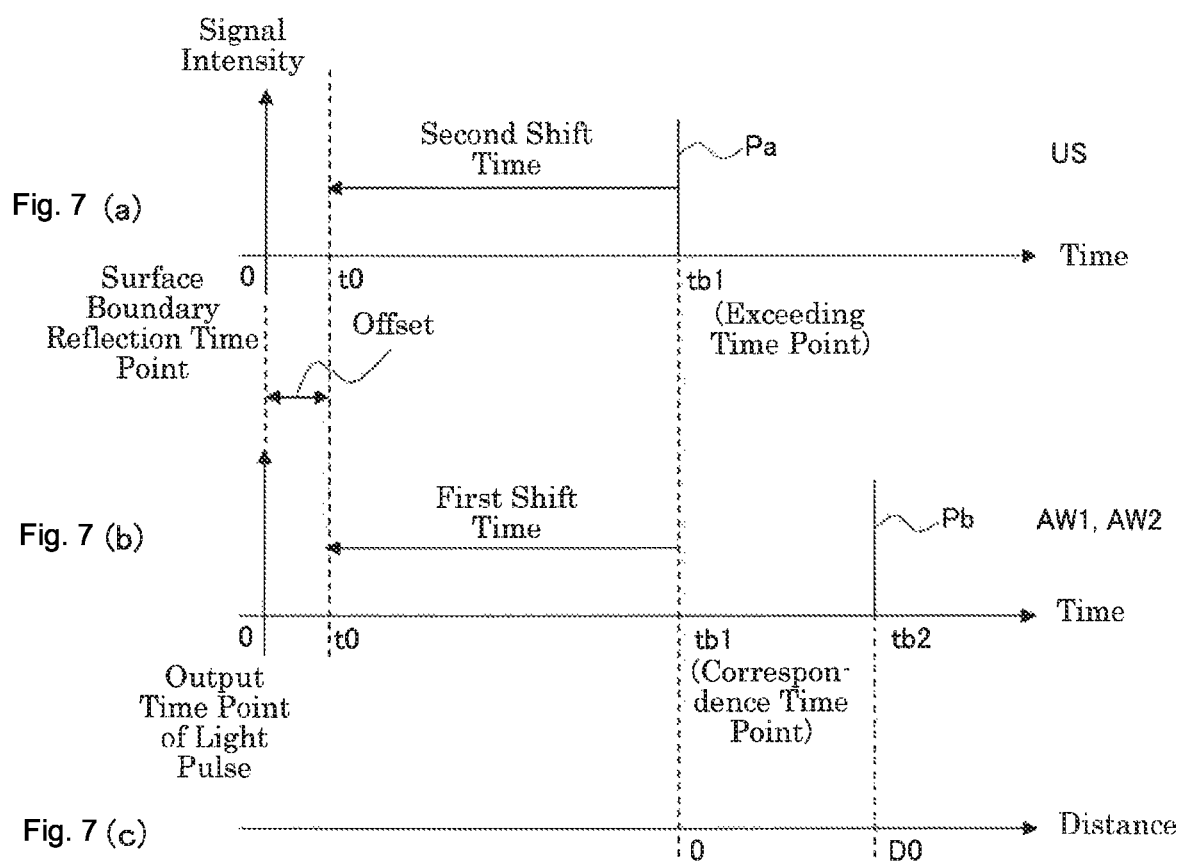
FIGS. 7 (a)-7 (c) show a waveform of the reflected wave US (FIG. 7 (a)), a waveform of the optoacoustic wave AW1 (or AW2) (FIG. 7 (b)), and a distance-converted version of the horizontal axis (time) of the waveforms (FIG. 7 (c)) when the measuring unit 100 is directly above the blood vessel 24b.

FIG. 7 shows a waveform of the reflected wave US (FIG. 7 (a)), a waveform of the optoacoustic wave AW1 (or AW2) (FIG. 7 (b)), and a distance-converted version of the horizontal axis (time) of the waveforms (FIG. 7 (c)) when the measuring unit 100 is directly above the blood vessel 24b.

In FIG. 7 (a), the vertical axis represents signal intensity, while the horizontal axis represents time, with the origin representing the time point at which the ultrasonic pulse is reflected by the surface boundary 22. At the time point tb1 at which an ultrasonic pulse Pa is received by the reflected wave measuring section 106 of the measuring unit 100, the measurement result of the reflected wave US (i.e. the signal intensity of the ultrasonic pulse Pa) exceeds a predetermined threshold value. It is noted that the predetermined threshold value is set such that (1) the intensity of the reflected wave US, if reflected by the surface boundary 22, exceeds the predetermined threshold value, while (2) the intensity of the reflected wave US, if not reflected by the surface boundary 22, does not exceed the predetermined threshold value. The exceeding time point acquiring section 110 is arranged to acquire an exceeding time point tb1 at which the measurement result of the reflected wave US exceeds the predetermined threshold value.

Since the signal intensity of the ultrasonic pulse Pa exceeds the predetermined threshold value, it is recognized that the reflection by the surface boundary 22 is detected by the reflected wave measuring section 106 at the time point (exceeding time point tb1) at which the ultrasonic pulse Pa is received. Accordingly, the distance d0+(D1−D0) between the reflected wave measuring section 106 and the surface boundary 22 is obtained by multiplying the time (referred to as exceeding time) between the reflection of the ultrasonic pulse at the surface boundary 22 of the measuring target 2 and the exceeding time point tb1 by the speed of sound Vs (Vs·tb1=d0+(D1−D0)) (where the exceeding time is tb1).

In FIG. 7 (*b*), the vertical axis represents signal intensity, while the horizontal axis represents time, with the origin representing the time point at which the light pulse P1 (or P2) is output. The output light pulse P1 (or P2) reaches the blood vessel 24*b* at almost the same time as the output. Accordingly, the time point at which the light pulse P1 (or P2) is output can be viewed the same as the time point at which the optoacoustic wave AW1 (or AW2) is output. Note here that the origin in FIG. 7 (*b*) (the time point at which the light pulse P1 (or P2) is output) and the origin in FIG. 7 (*a*) (the time point at which the ultrasonic pulse is reflected by the surface boundary 22) are at the same time point. The time point at which the optoacoustic pulse Pb of the optoacoustic wave AW1 (or AW2) generated at the blood vessel 24*b* is received by the optoacoustic wave measuring section 108 of the measuring unit 100 is defined as tb2. This results in Vs·tb2=d0+(D1−D0)+D0=d0+D1.

FIG. 7 (*c*) provides a horizontal axis, showing that if the position corresponding to the exceeding time point tb1 (representing the position of the surface boundary 22) is set 0, the position corresponding to the time point tb2 at which the optoacoustic pulse Pb is received (representing the depth of the blood vessel 24*b*) is D0 (=Vs·(tb2−tb1)).

The measurement result shifting section 112 is arranged to shift the measurement result of the optoacoustic waves AW1, AW2 by a first shift time toward the time point of output of the light pulses (see FIG. 7 (*a*)). The time point in the measurement result of the optoacoustic wave AW1 (or AW2) corresponding to the exceeding time point tb1 is here defined as a correspondence time point. The first shift time is then equal to or shorter than a correspondence time between the time point of output of the light pulses and the correspondence time point. It is noted that since the origin in FIG. 7 (*b*) and the origin in FIG. 7 (*a*) are at the same time point, the correspondence time point is tb1, which is the same as the exceeding time point tb1. The correspondence time is thus tb1.

The measurement result shifting section 112 is arranged to shift the measurement result of the reflected wave US by a second shift time toward the time point of output of the ultrasonic pulse (see FIG. 7 (*b*)). It is noted that the time point of output of the ultrasonic pulse precedes the time point at which the ultrasonic pulse is reflected by the surface boundary 22. Accordingly, the measurement result of the reflected wave US, when shifted toward the time point of output of the ultrasonic pulse, will also be shifted toward the time point at which the ultrasonic pulse is reflected by the surface boundary 22. It is noted that the second shift time is equal to or shorter than the exceeding time tb1.

It is noted that the first shift time and the second shift time are equal to each other. The difference t0 between the correspondence time tb1 and the first shift time is also equal to the difference t0 between the exceeding time tb1 and the second shift time (called offset).

It is noted that the difference (offset) between the first shift time and the correspondence time is equal for multiple optoacoustic waves AW1 (or AW2) obtained for multiple sites (blood vessels 24*a* and 24*b*) in the measuring target 2. That is, the difference between the first shift time of the optoacoustic wave AW1 (or AW2) obtained for the blood vessel 24*a* in the measuring target 2 and the correspondence time ta1 (see FIG. 5 (*b*)) and the difference between the first shift time of the optoacoustic wave AW1 (or AW2) obtained for the blood vessel 24*b* in the measuring target 2 and the correspondence time tb1 (see FIG. 7 (*b*)) are both equal to t0.

The difference (offset) between the exceeding time and the second shift time is equal for multiple reflected waves US obtained for multiple sites (portions of the surface boundary 22 directly above the blood vessels 24*a* and 24*b*) in the measuring target 2. That is, the difference between the second shift time of the reflected wave US obtained for a portion of the surface boundary 22 directly above the blood vessel 24*a* in the measuring target 2 and the exceeding time ta1 (see FIG. 5 (*a*)) and the difference between the second shift time of the reflected wave US obtained for a portion of the surface boundary 22 directly above the blood vessel 24*b* in the measuring target 2 and the exceeding time tb1 (see FIG. 7 (*a*)) are both equal to t0.

It is noted that the offset t0 may be 0.

Figure 8:
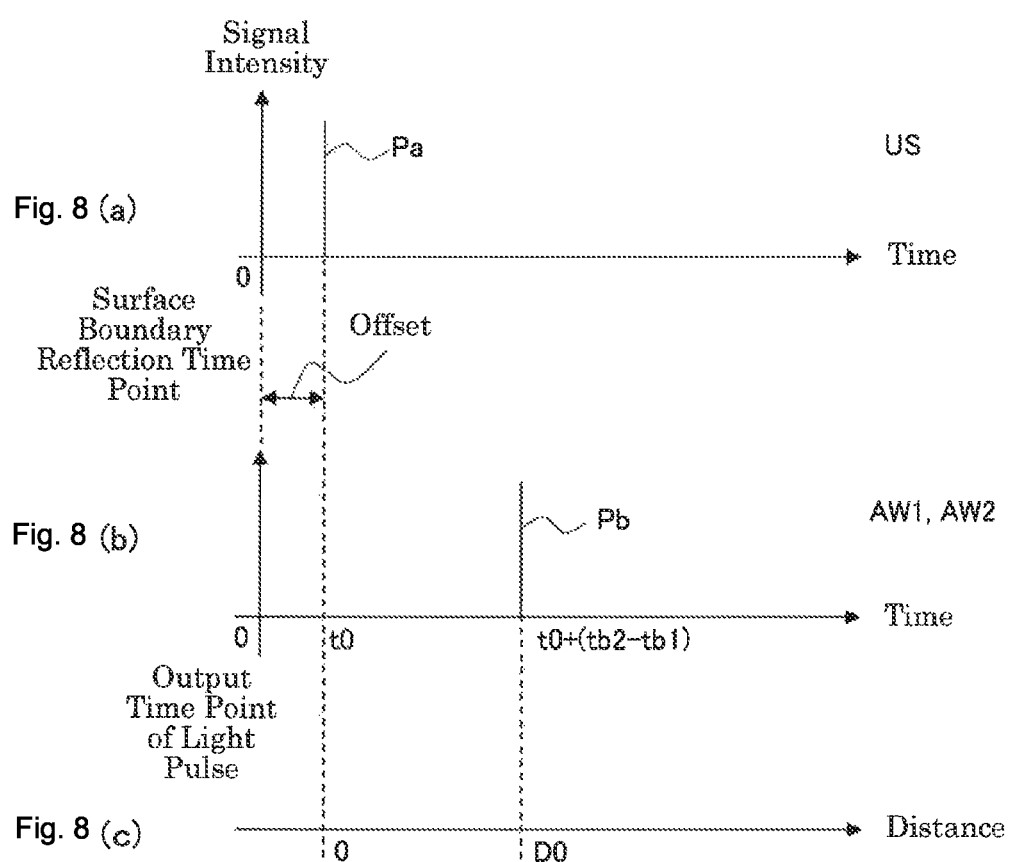
FIGS. 8 (a)-8 (c) show a shifted waveform of the reflected wave US according to FIG. 7 (a) (FIG. 8 (a)), a shifted waveform of the optoacoustic wave AW1 (or AW2) according to FIG. 7 (b) (FIG. 8 (b)), and a distance-converted version of the horizontal axis (time) of the waveforms (FIG. 8 (c))

FIG. 8 shows a shifted waveform of the reflected wave US according to FIG. 7 (*a*) (FIG. 8 (*a*)), a shifted waveform of the optoacoustic wave AW1 (or AW2) according to FIG. 7 (*b*) (FIG. 8 (*b*)), and a distance-converted version of the horizontal axis (time) of the waveforms (FIG. 8 (*c*)).

Referring to FIG. 8 (*a*), the measurement result shifting section 112 is arranged to shift the ultrasonic pulse Pa to the offset t0. Referring to FIG. 8 (*b*), the measurement result shifting section 112 is arranged to shift the optoacoustic pulse Pb to the time point t0+(tb2−tb1). FIG. 8 (*c*) provides a horizontal axis, showing that if the position corresponding to the offset t0 (representing the position of the surface boundary 22) is set 0, the position corresponding to the time point t0+(tb2−tb1) to which the optoacoustic pulse Pb is shifted (representing the depth of the blood vessel 24*b*) is D0 (=Vs·(t0+(tb2−tb1)−t0)=Vs·(tb2−tb1)).

Referring to FIG. 9, the upper end of the image corresponds to the origins in FIGS. 8 (*a*) and 8 (*b*). Here, the position corresponding to the offset t0 where the ultrasonic pulse Pa exists represents the position of the surface boundary 22. The image of the surface boundary 22 then exists at a position apart from the upper end of the image by Vs·t0. Further, the position corresponding to the time point t0+(tb2−tb1) where the optoacoustic pulse Pb exists represents the position of the blood vessel 24*b*. The image of the blood vessel 24*b* then exists at a position apart from the image of the surface boundary 22 by D0.

Next will be described an operation according to the embodiment of the present invention.

The measuring unit 100 scans the measuring target (skin) 2.

First of all, the measuring unit 100 moves to be almost directly above the blood vessel 24a (see FIGS. 11 (a) and 4).

An ultrasonic pulse output from the ultrasonic pulse output section 102 is reflected at the measuring target 2 and measured by the reflected wave measuring section 106 (reflected wave US) (see FIG. 5 (a)).

Optoacoustic waves AW1, AW2 generated at the measuring target 2 by light pulses output from the light pulse output sections 104a, 104b are measured by the optoacoustic wave measuring section 108 (see FIG. 5 (b)).

The signal intensity of an ultrasonic pulse Pa exceeds a predetermined threshold value. An exceeding time point ta1 at which a measurement result of the reflected wave US exceeds the predetermined threshold value is acquired by the exceeding time point acquiring section 110. The measurement result of the optoacoustic waves AW1, AW2 is shifted by a first shift time (shorter than the correspondence time ta1 by an offset t0) toward the time point of output of the light pulses by the measurement result shifting section 112 (see FIGS. 5 (b) and 6 (b)). The measurement result of the reflected wave US is also shifted by a second shift time (equal to the first shift time) toward the time point of output of the ultrasonic pulses (see FIGS. 5 (a) and 6 (a)).

The image displaying section 114 displays an image of the measuring target 2 (see FIG. 9) based on an output from the measurement result shifting section 112 (see FIGS. 6 (a) and 6 (b)).

The origins in FIGS. 6 (a) and 6 (b) then correspond to the upper end of the image in FIG. 9. The position corresponding to the offset t0 where the ultrasonic pulse Pa exists (the position apart from the upper end of the image by Vs·t0) represents the position of the surface boundary 22 in FIG. 9. The position corresponding to the time point t0+(ta2−ta1) where the optoacoustic pulse Pb exists (the position apart from the image of the surface boundary 22 by D0 (see FIG. 6 (c))) represents the position of the blood vessel 24a in FIG. 9.

Next, the measuring unit 100 moves to be almost directly above the blood vessel 24b (see FIGS. 11 (b) and 12).

An ultrasonic pulse output from the ultrasonic pulse output section 102 is reflected at the measuring target 2 and measured by the reflected wave measuring section 106 (reflected wave US) (see FIG. 7 (a)).

Optoacoustic waves AW1, AW2 generated at the measuring target 2 by light pulses output from the light pulse output sections 104a, 104b are measured by the optoacoustic wave measuring section 108 (see FIG. 7 (b)).

The signal intensity of the ultrasonic pulse Pa exceeds a predetermined threshold value. An exceeding time point tb1 at which a measurement result of the reflected wave US exceeds the predetermined threshold value is acquired by the exceeding time point acquiring section 110. The measurement result of the optoacoustic waves AW1, AW2 is shifted by a first shift time (shorter than the correspondence time tb1 by an offset t0) toward the time point of output of the light pulses by the measurement result shifting section 112 (see FIGS. 7 (b) and 8 (b)). The measurement result of the reflected wave US is also shifted by a second shift time (equal to the first shift time) toward the time point of output of the ultrasonic pulses (see FIGS. 7 (a) and 8 (a)).

The image displaying section 114 displays an image of the measuring target 2 (see FIG. 9) based on an output from the measurement result shifting section 112 (see FIGS. 8 (a) and 8 (b)).

The origins in FIGS. 8 (a) and 8 (b) then correspond to the upper end of the image in FIG. 9. The position corresponding to the offset t0 where the ultrasonic pulse Pa exists (the position apart from the upper end of the image by Vs·t0) represents the position of the surface boundary 22 in FIG. 9. The position corresponding to the time point t0+(tb2−tb1) where the optoacoustic pulse Pb exists (the position apart from the image of the surface boundary 22 by D0 (see FIG. 8 (c))) represents the position of the blood vessel 24b in FIG. 9.

The operation when the measuring unit 100 is almost directly above the blood vessel 24c is identical to the operation when the measuring unit 100 is almost directly above the blood vessel 24b and therefore will not be described.

In accordance with the embodiment of the present invention, it is possible to measure the measuring target (skin) 2 while compensating for fluctuation in the surface profile (bulging) of the measuring target 2 when the optical ultrasonic wave measuring apparatus 1 is brought into contact with the measuring target 2.

That is, with nothing in contact with the measuring target 2, the surface boundary 22 of the measuring target 2 is horizontal and the blood vessels 24a, 24b, 24c all have a depth of D0 (see FIG. 2). On the other hand, when the optical ultrasonic wave measuring apparatus 1 is brought into contact with the measuring target 2, the surface boundary 22 of the measuring target 2 bulges (see FIGS. 3 and 11) and thereby the blood vessel 24a may have a position higher than those of the blood vessel 24b and the blood vessel 24c.

However, since ultrasonic pulses Pa obtained as a result of reflection of an ultrasonic pulse at the surface boundary 22 directly above the blood vessels 24a, 24b (and also 24c) are both shifted to the offset t0 (see FIGS. 6 (a) and 8 (a)) (by a second shift time), the surface boundary 22 is displayed horizontally (see FIG. 9). In addition, since an optoacoustic pulse Pb of an optoacoustic wave AW1 (or AW2) obtained from the blood vessels 24a, 24b (and also 24c) is also shifted by the same time (first shift time (equal to the second shift time)) (see FIGS. 6 (b) and 8 (b)), the blood vessels 24a, 24b (and also 24c) are both displayed to have a depth of D0 (see FIG. 9).

Incidentally, the above-described embodiment may be achieved as follows. A computer including a CPU, a hard disk, and a medium (USB memory, CD-ROM, or the like) reading device is caused to read a medium with a program recorded thereon that achieves the above-described components (e.g. exceeding time point acquiring section 110, measurement result shifting section 112, and image displaying section 114) and install the program in the hard disk. The above-described features can also be achieved in this manner.

DESCRIPTION OF REFERENCE NUMERAL

1 Optical Ultrasonic Wave Measuring Apparatus
100 Measuring Unit
102 Ultrasonic Pulse Output Section
104a, 104b Light Pulse Output Sections
106 Reflected Wave Measuring Section
108 Optoacoustic Wave Measuring Section
110 Exceeding Time Point Acquiring Section
112 Measurement Result Shifting Section
114 Image Displaying Section
120 Case
130 Liquid
140 Chassis 2 Measuring Target (Skin)
22 Surface Boundary
24a, 24b, 24c Blood Vessel
US Reflected Wave
AW1, AW2 Optoacoustic Wave
Pa Ultrasonic Pulse
Pb Optoacoustic Pulse
D0 Depth
t0 Offset

What is claimed is:

1. An optical ultrasonic wave measuring apparatus comprising:
    an ultrasonic pulse output section arranged to output an ultrasonic pulse;
    a light pulse output section arranged to output a light pulse;
    a reflected wave measuring section arranged to measure, in correspondence to time, a reflected wave as a result of reflection of the ultrasonic pulse at a measuring target;
    an optoacoustic wave measuring section arranged to measure, in correspondence to time, an optoacoustic wave generated by the light pulse at the measuring target;
    an exceeding time point acquiring section arranged to acquire an exceeding time point at which a measurement result of the reflected wave exceeds a predetermined threshold value, wherein the exceeding time point is defined as an end point of a time-period that begins with the ultrasonic pulse being reflected at the measuring target and ends with the reflected wave, resulting from the reflected ultrasonic pulse, being received by the reflected wave measuring section; and
    a measurement result shifting section arranged to shift a measurement result of the optoacoustic wave by a first shift time toward the time point of output of the light pulse, wherein
    in a state where the time point in the measurement result of the optoacoustic wave corresponding to the exceeding time point is defined as a correspondence time point, the first shift time is equal to or shorter than a correspondence time between the time point of output of the light pulse and the correspondence time point.

2. The optical ultrasonic wave measuring apparatus according to claim 1, wherein
    the difference between the first shift time and the correspondence time is equal for a plurality of optoacoustic waves obtained for a plurality of sites in the measuring target.

3. The optical ultrasonic wave measuring apparatus according to claim 1, wherein
    the measurement result shifting section is arranged to shift the measurement result of the reflected wave by a second shift time toward the time point of output of the ultrasonic pulse, and
    the second shift time is equal to or shorter than an exceeding time between the reflection of the ultrasonic pulse at the surface boundary of the measuring target and the exceeding time point.

4. The optical ultrasonic wave measuring apparatus according to claim 3, wherein
    the difference between the exceeding time and the second shift time is equal for a plurality of reflected waves obtained for a plurality of sites in the measuring target.

5. The optical ultrasonic wave measuring apparatus according to claim 3, wherein
    the first shift time and the second shift time are equal to each other.

6. The optical ultrasonic wave measuring apparatus according to claim 3, wherein
    the exceeding time point and the correspondence time point are at the same time point.

7. The optical ultrasonic wave measuring apparatus according to claim 1, further comprising an image displaying section arranged to display an image of the measuring target based on an output from the measurement result shifting section.

8. The optical ultrasonic wave measuring apparatus according to claim 1, wherein
    the ultrasonic pulse output section and the light pulse output section are arranged to scan the measuring target, and
    the direction of the scanning is orthogonal to the direction of output of the ultrasonic pulse and the light pulse.

9. The optical ultrasonic wave measuring apparatus according to claim 1, further comprising a plurality of light pulse output sections, wherein
    the light pulse output sections are arranged to output light pulses of different wavelengths.

10. An optical ultrasonic wave measuring method, comprising:
    outputting an ultrasonic pulse;
    outputting a light pulse;
    providing a reflected wave measuring section;
    measuring, in correspondence to time, a reflected wave as a result of reflection of the ultrasonic pulse at a measuring target;
    measuring, in correspondence to time, an optoacoustic wave generated by the light pulse at the measuring target;
    acquiring an exceeding time point at which a measurement result of the reflected wave exceeds a predetermined threshold value, the exceeding time point being defined as an end point of a time-period that begins with the ultrasonic pulse being reflected at the measuring target and ends with the reflected wave, resulting from the reflected ultrasonic pulse, being received by the reflected wave measuring section; and
    shifting a measurement result of the optoacoustic wave by a first shift time toward the time point of output of the light pulse, wherein
    in a state where the time point in the measurement result of the optoacoustic wave corresponding to the exceeding time point is defined as a correspondence time point, the first shift time is equal to or shorter than a correspondence time between the time point of output of the light pulse and the correspondence time point.

11. A non-transitory computer-readable medium having a program of instructions for execution by a computer to perform an optical ultrasonic wave measuring process of an optical ultrasonic wave measuring apparatus including: an ultrasonic pulse output section arranged to output an ultrasonic pulse; a light pulse output section arranged to output a light pulse; a reflected wave measuring section arranged to measure, in correspondence to time, a reflected wave as a result of reflection of the ultrasonic pulse at a measuring target; and an optoacoustic wave measuring section arranged to measure, in correspondence to time, an optoacoustic wave generated by the light pulse at the measuring target, the process comprising:
    acquiring an exceeding time point at which a measurement result of the reflected wave exceeds a predetermined threshold value, the exceeding time point being defined as an end point of a time-period that begins with the ultrasonic pulse being reflected at the measuring target and ends with the reflected wave, resulting from the reflected ultrasonic pulse, being received by the reflected wave measuring section; and shifting a measurement result of the optoacoustic wave by a first shift time toward the time point of output of the light pulse, wherein in a state where the time point in the measurement result of the optoacoustic wave corresponding to the exceeding time point is defined as a correspondence time point, the first shift time is equal to or shorter than a correspondence time between the time point of output of the light pulse and the correspondence time point.

\* \* \* \* \*